United States Patent [19]
Julian et al.

[11] Patent Number: 5,717,064
[45] Date of Patent: Feb. 10, 1998

[54] METHYLATED LYSINE-RICH LYTIC PEPTIDES AND METHOD OF MAKING SAME BY REDUCTIVE ALKYLATION

[75] Inventors: Gordon R. Julian, Bozeman, Mont.; Jesse M. Jaynes, Raleigh, N.C.

[73] Assignee: Demeter Biotechnologies, Ltd., Durham, N.C.

[21] Appl. No.: 427,001

[22] Filed: Apr. 24, 1995

Related U.S. Application Data

[63] Continuation-in-part of Ser. No. 148,889, Nov. 18, 1993, abandoned.
[51] Int. Cl.$^6$ .............................. C07K 5/00; C07K 7/00; C07K 17/00; A61K 38/00
[52] U.S. Cl. ............................................. 530/324; 514/12
[58] Field of Search ............................... 514/12; 530/324

[56] References Cited

U.S. PATENT DOCUMENTS

| | | | |
|---|---|---|---|
| 4,355,104 | 10/1982 | Hultmark et al. | 435/70 |
| 4,520,016 | 5/1985 | Hultmark et al. | 514/12 |
| 4,810,777 | 3/1989 | Zasloff | 530/326 |
| 5,045,531 | 9/1991 | Berkowitz et al. | 514/12 |
| 5,059,653 | 10/1991 | Coy et al. | . |
| 5,114,921 | 5/1992 | Zasloff | 514/12 |
| 5,217,956 | 6/1993 | Zasloff et al. | 514/13 |

FOREIGN PATENT DOCUMENTS 9012866 11/1990 WIPO.

OTHER PUBLICATIONS

Jaynes, "Lytic Peptides Portend an Innovative Age in the Management and Treatment of Human Disease", Drug News and Perspectives, 3 (1990).
Arrowood et al., "Hemolytic Properties of Lytic Peptides Active Against the Sporozoites of Cryptosporidium parvum", J. Protozool, 38 (1991).
Jaynes et al., "In Vitro Cytocidal Effect of Lytic Peptides on Several Transformed Mammalian Cell Lines", Peptide Research 2 (1989) pp. 157–160.
Jaynes et al., "In Vitro Effect of Novel Lytic Peptides on Plasmodium falciparum and Trypanosoma cruzi", FASEB J. 2 (1988) pp. 2878–2883.
Reed et al., "Enhanced in vitro Growth of Murine Fibroblast Cells and Preimplantation Embryos Cultured in Medium Supplemented with an Amphipathic Peptide", Molecular Reproduction and Development 31 (1992) pp. 106–113.
Akerfeldt et al., "Synthetic Peptides as Models for Ion Channel Proteins", Acc. Chem. Res. 26 (1993) pp. 191–197.
Wong et al., "Pyridine Borane as a Reducing Agent for Proteins", Anal. Biochem. 139 (1984) pp. 58–67.
Means et al., "Reductive Alkylation of Amino Groups in Proteins", Biochemistry 7 (1968) pp. 2192–2201.
Lilova et al., "Reductive Alkylation of Lysine Residues in Subtilisin DY", Biol. Chem. Hoppe–Seyler, 368 (1987) pp. 1479–1487.
Boarder et al., "Synthetic N–Dimethyl Beta–Endorphin, A Stabilized Opioid Peptide", Biochemical Pharmacology, 30 (1981), pp. 1289–1293.
Habeeb, "Determination of Free Amino Groups in Proteins by Trinitrobenzene–sulfonic Acid", Anal. Biochem. 14 (1966) pp. 328–336.
Gorecki et al., "Non Cationic Substrates of Trypsin", Biochem. and Biophys. Res. Comm. 29 (1967), pp. 189–193.

*Primary Examiner*—Toni R. Scheiner
*Assistant Examiner*—Sheela J. Huff
*Attorney, Agent, or Firm*—Rothwell, Figg, Ernst & Kurz

[57] ABSTRACT

A tryptic digestion-resistant, non-naturally occurring lytic peptide comprising a sequence of amino acid residues containing mainly alanine, valine and lysine amino acid residues, wherein the ε-amino groups of the lysine residues and the α-amino group of the N-terminal amino acid are sufficiently methylated to impart enhanced tryptic, chymotryptic, and aminopeptidase digestion resistance to the peptide. The secondary conformation of the peptide is an ordered periodic structure such as an amphipathic α-helix or a β-pleated sheet. The compositions of the invention are suitable for in vivo administration.

A method of making the same, to impart enhanced tryptic digestion-resistance thereto, comprising reductively alkylating the ε-amino groups of the lysine residues and the α-amino group of the N-terminal amino acid with a methylproviding reagent in the presence of an heterocyclic amineborane reducing agent for sufficient time and at sufficient conditions to methylate the α-and ε-amino groups to sufficient extent to confer enhanced proteolytic digestion-resistance to the peptide.

8 Claims, 3 Drawing Sheets

METHYLATED LYSINE-RICH LYTIC PEPTIDES AND METHOD OF MAKING SAME BY REDUCTIVE ALKYLATION

This is a continuation-in-part of application No. 08/148,889, filed Nov. 8, 1993, now abandoned.

BACKGROUND OF THE INVENTION

1. Field of the Invention

The present invention relates to methylation-stabilized, lysine-rich synthetic lytic peptide compositions with enhanced resistance to proteolytic digestion, and to methods of making the same.

2. Description of Related Art

Naturally occurring lytic peptides play an important if not critical role as immunological agents in insects and have some, albeit secondary, defense functions in a range of other animals. The function of these peptides is to destroy prokaryotic and other non-host cells by disrupting the cell membrane and promoting cell lysis. Common features of these naturally occurring lytic peptides include an overall basic charge, a small size (23–39 amino acid residues), and the ability to form amphipathic α-helices. Several types of naturally occurring lytic peptides have been identified: cecropins (described in U.S. Pat. Nos. 4,355,104 and 4,520,016 to Hultmark et al.), defensins, sarcotoxins, melittin, and magainins (described in U.S. Pat. No. 4,810,777 to Zasloff). Each of these peptide types is distinguished by sequence and secondary structure characteristics.

Several hypotheses have been suggested for the mechanism of action of the lytic peptides: disruption of the membrane lipid bilayer by the amphipathic α-helix portion of the lytic peptide; lytic peptide formation of ion channels, which results in osmotically induced cytolysis; lytic peptide promotion of protein aggregation, which results in ion channel formation; and lytic peptide-induced release of phospholipids. Whatever the mechanism of lytic peptide-induced membrane damage, an ordered secondary conformation such as an amphipathic α-helix and positive charge density are features that appear to participate in the function of the lytic peptides.

Active analogs of naturally occurring lytic peptides have been produced and tested in vitro against a variety of prokaryotic and eukaryotic cell types (see for example Arrowood, M. J., et al., J. Protozool. 38: 161s [1991]; Jaynes, J. M., et al., FASEB J. 2:2878 [1988]), including: gram positive and gram negative bacteria, fungi, yeast, envelope viruses, virus-infected eukaryotic cells, and neoplastic or transformed mammalian cells. The results from these studies indicate that many of the synthetic lytic peptide analogs have similar or higher levels of lytic activity for many different types of cells, compared to the naturally occurring forms. In addition, the peptide concentration required to lyse microbial pathogens such as protozoans, yeast, and bacteria does not lyse normal mammalian cells.

The specificity of the lytic action depends upon the sequence and structure of the peptide, the concentration of the peptide, and the type of membrane with which it interacts. Jaynes J. M. et al., Peptide Research 2: 157 (1989) discuss the altered cytoskeletal characteristics of transformed or neoplastic mammalian cells that make them susceptible to lysis by the peptides. In these experiments, normal, human non-transformed cells remained unaffected at a given peptide concentration while transformed cells were lysed; however, when normal cells were treated with the cytoskeletal inhibitors cytochalasin D or colchicine, sensitivity to lysis increased. The experiments show that the action of lytic peptides on normal mammalian cells is limited. This resistance to lysis was most probably due to the well-developed cytoskeletal network of normal cells. In contrast, transformed cell lines which have well-known cytoskeletal deficiencies were sensitive to lysis. Because of differences in cellular sensitivity to lysis, lytic peptide concentration can be manipulated to effect lysis of one cell type but not another at the same locus.

Synthetic lytic peptide analogs can also act as agents of eukaryotic cell proliferation. Peptides that promote lysis of transformed cells will, at lower concentrations, promote cell proliferation in some cell types. This stimulatory activity is thought to depend on the channel-forming capability of the peptides, which somehow stimulates nutrient uptake, calcium influx or metabolite release, thereby stimulating cell proliferation (see Jaynes, J. M. Drug News & Perspectives 3: 69 [1990]; and Reed, W. A. et al., Molecular Reproduction and Development 31: 106 [1992]). Thus, at a given concentration, these peptides stimulate or create channels that can be beneficial to the normal mammalian cell in a benign environment where it is not important to exclude toxic compounds.

The synthetic lytic peptide analogs according to the present invention typically contain as few as 12 and as many as 40 amino acid residues. A phenylalanine residue is often positioned at the amino terminus of the protein to provide an aromatic moiety analogous to the tryptophan residue located near the amino terminus of natural cecropins and a UV-absorbing moiety with which to monitor the purification of the synthetic peptide. The basis for the design of these lytic peptide analogs is that a peptide of minimal length, having an amphipathic s-helical structural motif, and overall positive charge density effects lytic activity. Peptides that have the structural motif of a β-pleated sheet and overall positive charge density can also effect lytic activity.

As discussed above, in vitro laboratory tests of the lytic peptide analogs have been successful. However, the use of the lytic peptide analogs in vivo could be considerably limited in circumstances where proteases may digest the peptide analogs before sufficient pathogen cell lysis has occurred. In particular, the high concentration of positively charged amino acids such as lysine and arginine make the synthetic peptides susceptible to tryptic digestion. The secondary conformation of the peptides sequesters the hydrophobic amino acid residues, thus shielding them from interaction with proteases such as chymotrypsin, which hydrolyzes peptides at bulky or aromatic amino acid residues. This proteolytic susceptibility is a general problem for peptides and proteins when used in vivo. Many techniques are suitable for stabilizing proteins to tryptic digestion for in vitro use but are not appropriate for in vivo or oral administration to humans and animals.

Several studies teach that modification by methylation of the N-terminal α-amino group in a protein or peptide has been used to study structure-function relationships in a variety of naturally occurring proteins and their substrates or receptors.

Means, G. E. et al., Biochemistry 7:2192 (1968) teach that when proteins are treated with aldehydes or ketones and sodium borohydride, amino groups are converted into corresponding mono- or dialkylamino derivatives. Trypsin attacks proteins and peptides at the positively charged lysine and arginine residues. Dimethylation of the ε-amino group of lysine residues renders some modified proteins essentially resistant to tryptic digestion, however, in this study, the test enzyme ribonuclease was enzymatically inactivated by the modification.

Lilova, A. et al., Biol. Chem. Hoppe-Seyler 368: 1479 (1987) teach that methylation of ε-amino groups of lysine residues can be used to determine the essential nature of lysine residues in the maintenance of biological activity. This report states that the lysine residues in the test protein (subtilisin DY) do not participate directly in the catalytic reaction.

Boarder et al., Biochem. Pharmacol. 30: 1289 (1981) teach that the N-terminal α-amino group and the ε-amino group of lysine residues in β-endorphin, a naturally occurring opioid peptide, can be dimethylated using formaldehyde and sodium cyanoborohydride, providing resistance to tryptic and aminopeptidase digestion. The authors speculate that the naturally occurring, modified β-endorphin may have a longer half-life in vivo. As a basis for this speculation the authors cite Hammond et al., 1979, in which the authors report that for β-endorphin, receptor binding is maintained after lysine ε-amino dimethylation. However, this statement of retained receptor affinity cannot be extrapolated to predict bioreactivity of the methylated derivative. The biological activity of the modified β-endorphin was tested in neither case.

Coy et al., U.S. Pat. No. 5,059,653 teach a solid state method using sodium cyanoborohydride and carbonyl-containing compounds to modify the ε-amino group of lysine residues to provide proteolytic stability for proteins. However, the use of sodium cyanoborohydride introduces into the preparation a potential cyanide contamination that may be detrimental for in vivo usage. Furthermore, this method does not address retention of biological activity.

Accordingly, it would be a significant advance in the art to provide a method of producing methylated physiologically active lytic peptides that have enhanced resistance to proteolysis.

It would be particularly desirable to provide a method of producing such peptides so that the methylated peptides have enhanced proteolytic stability and retain their physiological activity for in vivo applications against pathogenic microbial organisms such as bacteria, yeast, fungi, and protozoans; neoplastic or transformed cells; envelope viruses; and virally-infected cells.

These and other objects and advantages will be more fully apparent from the ensuing disclosure and claims.

SUMMARY OF THE INVENTION

The present invention relates generally to methylation-stabilized, lysine-rich synthetic lytic peptide compositions with enhanced resistance to proteolytic digestion, and to methods of making the same.

More specifically, the present invention relates in a broad compositional aspect to chemically modified, lysine-rich synthetic peptides with an overall positive charge density, wherein the ε-amino groups of lysine residues and the N-terminal α-amino group are dimethylated by a method of reductive alkylation.

In one particular aspect, the present invention relates to a physiologically active peptide composition comprising a synthetic physiologically active peptide that has been chemically modified, wherein the ε-amino groups of lysine residues and the N-terminal α-amino group are sufficiently methylated such that the chemically modified physiologically active peptide has enhanced in vivo resistance to enzymatic digestion, relative to the physiologically active peptide alone.

In another aspect, the present invention relates to a group of similar physiologically active peptide compositions, comprising: (i) physiologically active synthetic peptides that have been chemically modified, wherein the ε-amino groups of lysine residues and the N-terminal α-amino group are dimethylated; and (ii) chemically modified, physiologically active synthetic peptides that are related by amino acid sequence and physiological activity.

In another aspect, the invention relates to a physiologically active peptide composition comprising synthetic peptides which contain as few as 12 and as many as 40 amino acid residues, wherein the peptide is comprised mainly of three amino acid monomers: alanine, valine and lysine. A phenylalanine residue is present at or near the N-terminus of the peptide. Cysteine or serine amino acid residues are present in five of the peptides and have chemically masked side chain groups.

The invention relates in a further aspect to a physiologically active peptide composition comprising a physiologically active synthetic peptide that has been chemically modified, wherein the ε-amino groups of lysine residues and the N-terminal α-amino group are dimethylated. In such a peptide, the secondary conformation of the peptide is in a periodic structural motif, an amphipathic α-helix, in which one side of the cylinder is hydrophilic, with the polar amino acid residues exposed on this surface. The other side of the cylinder is hydrophobic, with the side chains of the hydrophobic amino acid residues seeking an anhydrous environment. Serine residues may be exposed on either surface.

The invention relates in a further aspect to a physiologically active peptide composition comprising a physiologically active synthetic peptide that has been chemically modified, wherein the ε-amino groups of lysine residues and the N-terminal α-amino group are dimethylated. In such a peptide, the secondary conformation of the peptide is in a periodic structural motif, the β-pleated sheet, in which the polypeptide chain is extended in a sheet-like conformation rather than a cylinder-like conformation.

The invention relates in yet a further aspect to a physiologically active peptide composition comprising a physiologically active synthetic peptide that has been chemically modified, wherein the ε-amino groups of lysine residues and the N-terminal α-amino group are dimethylated. In such a peptide, the secondary conformation is an amphipathic α-helix. With such a conformation in an aqueous environment, the hydrophobic regions would adhere to each other to form micelles and hence isolated domains of a separate phase. Only the dimethylated lysine side chain residues that are hydrophilic but have enhanced resistance to tryptic hydrolysis are exposed to the aqueous environment, and hence to proteolytic enzymes.

The invention relates in yet a further aspect to a physiologically active peptide composition comprising a physiologically active synthetic peptide that has been chemically modified, wherein the ε-amino groups of lysine residues and the N-terminal α-amino group are dimethylated. In such a peptide, the secondary conformation of the peptide is in a periodic structural motif, the β-pleated sheet. In such a configuration, individual polypeptides can associate into overlapping structures. This association is stabilized by hydrogen bond formation between NH and CO groups in separate polypeptide strands The invention relates in a further aspect to a physiologically active peptide composition comprising a physiologically active synthetic peptide that has been chemically modified, wherein the ε-amino groups of lysine residues and the N-terminal α-amino group are dimethylated. Such a peptide is used in vivo to treat infections caused by pathogenic microbial organisms such as bacteria, yeast, fungi, and protozoans by lysing these organisms; to treat cancers caused by neoplastic or transformed cells by lysing such cells; and to treat viral infections by lysing envelope viruses and virally-infected cells.

The term "amphipathic" as used herein refers to the distribution of hydrophobic and hydrophilic amino acid residues along opposing faces of an α-helix structure or other secondary conformation, which results in one face of the α-helix structure being predominantly hydrophobic and the other face being predominantly hydrophilic. The degree of amphipathy of a peptide can be assessed by plotting the sequential amino acid residues on an Edmunson helical wheel.

The term "peptide" as used herein is intended to be broadly construed as inclusive of polypeptides per se having molecular weights of up to 10,000 daltons, as well as proteins having molecular weights of greater that about 10,000 daltons, wherein the molecular weights are number average molecular weights.

The term "methylated" as used herein means that the specified amino groups have been chemically reacted by a method of reductive alkylation or methylation so that the associated hydrogen atoms are replaced by covalently coupled methyl groups.

DETAILED DESCRIPTION OF THE INVENTION AND PREFERRED EMBODIMENTS THEREOF

Figure 1:
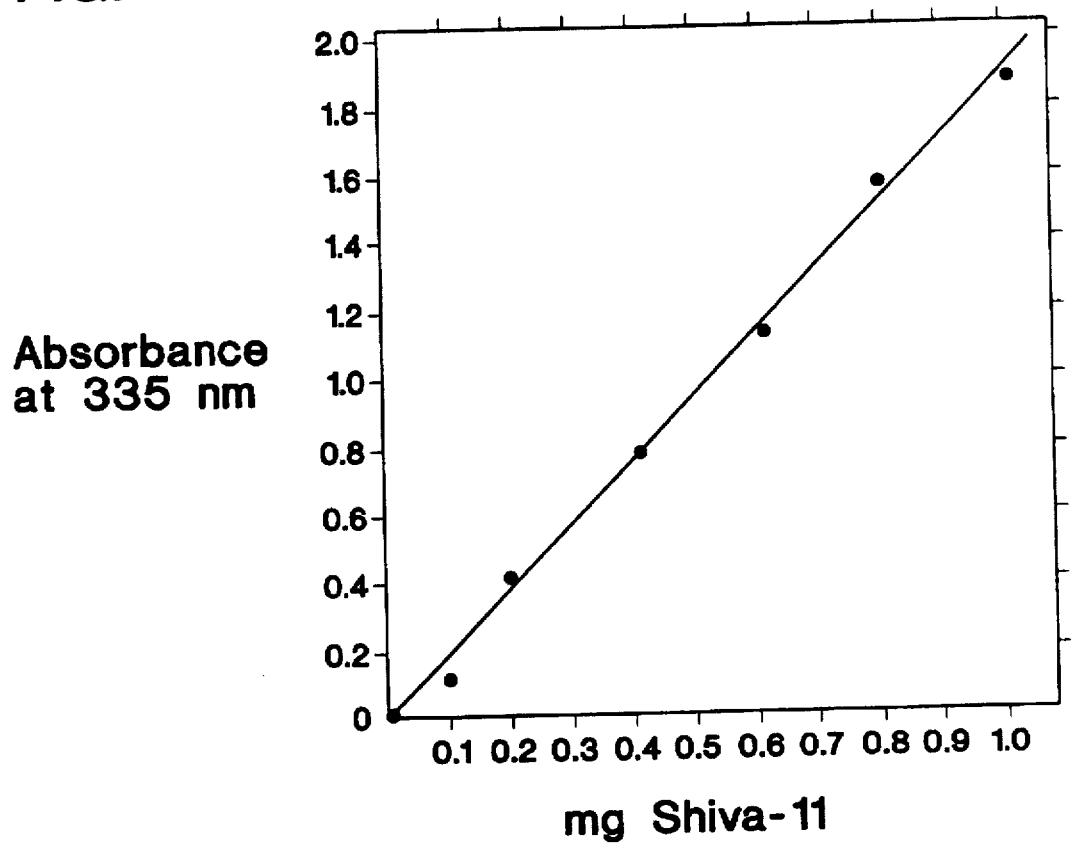
FIG. 1 shows the TNBS assay standard curve for unmodified peptide Shiva-11.

Chemical modification of lytic peptide analogs offers certain advantages. If the modifications are made in such a way that the lytic peptides retain all or most of their biological activity, then the following advantage results: the peptides have enhanced stability to proteolysis. With enhanced stability, the peptides can be administered in vivo without loss of biological activity through proteolytic digestion.

The chemical modification of lysine rich lytic peptide analogs by methylation of the ε-amino groups of lysine residues and the N-terminal α-amino group achieves in vivo stabilization against tryptic attack while preserving biological activity.

When considering lytic peptide analog stabilization with chemical modification of amino acid residue side chains, it is important to consider the character (hydrophobic or hydrophilic) and location of the individual amino acids residues within the peptides of concern. With the lytic peptide analogs proposed herein, the following are the only types of amino acid residues to be examined: phenylalanine, alanine, valine, lysine, cysteine, and serine. Of this group, serine and lysine are potentially exposed to proteases in the aqueous environment, as a result of the secondary conformation of the peptide. In peptides containing serine or cysteine, these groups could be previously chemically modified to mask amino acid residue.

The lytic peptide analogs are designed to take the configuration of an amphipathic α-helix structure or, in the case of SEQ ID 30–38, a β-pleated sheet conformation. In an aqueous environment the hydrophobic regions of these peptides would adhere to each other, forming micelles and hence isolated domains of a separate phase. In this circumstance, the hydrophobic moieties would be unavailable to the aqueous phase and hence to hydrolysis by proteolytic enzymes. In one preferred aspect of the invention, the lytic peptides assume the secondary conformation of an amphipathic α-helix.

Each lysine side chain contains an ε-amino group ($-NH_3^+$) which provides the peptide with a unit positive charge at physiological pH. The combined charges from the multiple lysine side chains contribute to the polarity and thus the regional hydrophilicity required for formation of an amphipathic α-helix. The positive charge of these lytic peptide analogs is required for activity. Amphipathy alone does not provide for lytic action, thus the SEQ ID 30–38 peptides in the β-pleated sheet conformation with an overall positive charge density also have lytic activity. Modification of the ε-amino group of the lysine amino acid residue does not affect the unit charge of the lysine residue or the peptide. However, susceptibility to tryptic hydrolysis for the lysine residue α-carbonyl peptide linkages is drastically reduced.

As discussed above, it can be presumed that alanine, valine, internal phenylalanine, cysteine, and serine contained in the lytic peptide analogs are not vulnerable to proteolytic attack due to their removal from the aqueous phase or prior chemical masking. Lysine, however, provides a specific locus for the most aggressive proteolytic enzyme, trypsin. For this reason, reductive alkylation of the lytic peptides would provide enhanced stability to proteolytic hydrolysis. It should also be noted that the N-terminal α-amino group is also exposed and would also become alkylated during such a procedure, thus providing further resistance to both chymotrypsin, which attacks aromatic amino acids such as phenylalanine, and aminopeptidases, which act at the N-terminus.

One objective of the present invention is to provide enhanced proteolytic stability to a series of lysine-rich, lytic peptide analogs. Another objective is to use such modified lytic peptides for in vivo delivery of physiologically effective lytic peptides.

The features and advantages of the invention are more fully shown by the following illustrative examples and embodiments, which are not to be limitingly construed as regards the broad scope, utility, and applicability of the invention.

EXAMPLE 1

Representative Lytic Peptides

Set out in Table 1 below as illustrative examples of lytic peptide analogs of the present invention are the amino acid sequences of a family of related peptide analogs. The peptides may be synthesized according to conventional methods using a Milligen™ solid phase peptide synthesizer. Representative peptides from this group are methylated, and used in subsequent experimental examples. The three letter amino acid symbols are as follows: Ala, alanine; Cys, cysteine; Lys, lysine; Phe, phenylalanine; Ser, serine; and Val, valine. These lytic peptide analogs are designated for ease of reference as SEQ ID NO. 1–6 and 14–43.

TABLE 1

PEPTIDE SEQUENCES

SEQ ID NO. 1: Phe Ala Val Ala Val Lys Ala Val Lys Lys Ala Val Lys Lys Val Lys Lys Ala Val Lys Lys Ala Val Lys Lys Lys Lys

SEQ ID NO. 2: Phe Ala Val Ala Val Lys Ala Val Ala Val Lys Ala Val Lys Lys Ala Val Lys Lys Val Lys Lys Ala Val Lys Lys Ala Val Lys Lys Lys

SEQ ID NO. 3: Phe Ala Val Ala Val Lys Ala Val Ala Val Lys Ala Val Ala Val Lys Ala Val Lys Lys Ala Val Lys Lys Val Lys Lys Val Lys Lys Ala Val Lys Lys Ala Val Lys Lys Lys

SEQ ID NO. 4: Phe Ala Val Ala Val Lys Ala Val Lys Lys Ala Val Lys Lys Val Lys Lys Ala Val Lys Lys Ala Val

SEQ ID NO. 5: Phe Ala Val Ala Val Lys Ala Val Ala Val Lys Ala Val Lys Lys Ala Val Lys Lys Val Lys Lys Ala Val Lys Lys Ala Val

SEQ ID NO. 6: Phe Ala Val Ala Val Lys Ala Val Ala Val Lys Ala Val Ala Val Lys Ala Val Lys Lys Ala Val Lys Lys Val Lys Lys Ala Val Lys Lys Ala Val

SEQ. ID NO. 14: Ala Val Lys Arg Val Gly Arg Arg Leu Lys Lys Leu Ala Arg Lys Iso Ala Arg Leu Gly Val Ala Phe

SEQ ID NO. 15: Lys Lys Lys Lys Phe Val Lys Lys Val Ala Lys Lys Val Lys Lys Val Ala Lys Lys Val Ala Lys Val Ala Val Ala Val

SEQ ID NO. 16: Lys Lys Lys Lys Phe Val Lys Lys Val Ala Lys Lys Val Lys Lys Val Ala Lys Lys Val Ala Lys Val Ala Val Ala Lys Val Ala Val Ala Val

SEQ ID NO. 17: Lys Lys Lys Lys Phe Val Lys Lys Val Ala Lys Lys Val Lys Lys Val Ala Lys Lys Val Ala Lys Val Ala Val Ala Lys Val Ala Val Ala Lys Val Ala Val Ala Lys Val Ala Val Ala Val

SEQ ID NO. 18: Phe Val Lys Lys Val Ala Lys Lys Val Lys Lys Val Ala Lys Val Ala Lys Val Ala Val Ala Val

SEQ ID NO. 19: Phe Val Lys Lys Val Ala Lys Lys Val Lys Lys Val Ala Lys Val Ala Lys Val Ala Lys Val Ala Lys Val Ala Val Ala Val

SEQ ID NO. 20: Phe Val Lys Lys Val Ala Lys Lys Val Lys Lys Val Ala Lys Val Ala Lys Val Ala Lys Val Ala Lys Val Ala Lys Val Ala Val Ala Val

SEQ ID NO. 21: Lys Lys Lys Lys Phe Val Lys Lys Val Ala Lys Val Ala Lys Lys Val Ala Lys Val Ala Lys Lys Val Ala Lys Lys Val

SEQ ID NO. 22: Lys Lys Lys Lys Phe Val Lys Lys Val Ala Lys Lys Val Ala Lys Val Ala Lys Lys Val Ala Lys Val Ala Lys Lys Val Ala Lys Lys Val Ala Lys Lys Val Ala Lys Lys Val Ala

SEQ ID NO. 23: Lys Lys Lys Lys Phe Val Lys Lys Val Ala Lys Lys Val Ala Lys Val Ala Lys Lys Val Ala Lys Lys Val Ala Lys Lys Val Ala Lys Val Ala Lys Val Ala Lys Lys

SEQ ID NO. 24: Phe Val Lys Lys Val Ala Lys Val Ala Lys Lys Val Ala Lys Val Ala Lys Lys Val Ala Lys Lys Val

SEQ ID NO. 25: Phe Val Lys Lys Val Ala Lys Val Ala Lys Lys Val Ala Lys Val Ala Lys Lys Val Ala Lys Lys Val Ala Lys Lys Val Ala

SEQ ID NO. 26: Phe Val Lys Lys Val Ala Lys Val Ala Lys Val Ala Lys Lys Val Ala Lys Lys Val Ala Lys Lys Val Ala Lys Lys Val Ala Lys Lys

SEQ ID NO. 27: Phe Val Lys Lys Val Ala Lys Val Ala Lys Lys Val Ala Lys Lys Val Lys Lys Lys Lys

SEQ ID NO. 28: Phe Val Lys Lys Val Ala Lys Val Ala Lys Lys Val Ala Lys Lys Val Ala Lys Lys Val Ala Lys Lys Val Ala Lys Lys Val Ala Lys Lys Lys Lys Lys

SEQ ID NO. 29: Phe Val Lys Lys Val Ala Lys Val Ala Lys Lys Val Ala Lys Lys Val Ala Lys Lys Val Ala Lys Lys Val Ala Lys Lys Val Ala Lys Lys Lys Lys Lys

SEQ ID NO. 30: Phe Lys Val Lys Ala Lys Val Lys Ala Lys Val Lys Lys Lys Lys Lys

SEQ ID NO. 31: Phe Lys Val Lys Ala Lys Val Lys Ala Lys Val Lys Ala Lys Val Lys Ala Lys Lys Lys

SEQ ID NO. 32: Phe Lys Val Lys Ala Lys Val Lys Ala Lys Val Lys Ala Lys Val Lys Ala Lys Val Lys Lys Lys Lys

SEQ ID NO. 33: Phe Lys Val Lys Ala Lys Val Lys Ala Lys Val Lys

SEQ ID NO. 34: Phe Lys Val Lys Ala Lys Val Lys Ala Lys Val Lys Lys Ala Lys Val Lys Ala

SEQ ID NO. 35: Phe Lys Val Lys Ala Lys Val Lys Ala Lys Val Lys Ala Lys Val Lys Ala Lys Val Lys Ala Lys Val

SEQ ID NO. 36: Lys Lys Lys Lys Phe Lys Val Ala Lys Val Lys Ala Lys Val Lys

SEQ ID NO. 37: Lys Lys Lys Lys Phe Lys Val Lys Ala Lys Val Lys Ala Lys Val Lys Ala Lys Val Lys Ala

SEQ ID NO. 38: Lys Lys Lys Lys Phe Lys Val Lys Ala Lys Val Lys Ala Lys Val Lys Ala Lys Val Ala Lys Val Ala Lys Val Lys Ala Lys Val

SEQ ID NO. 39: Phe Lys Lys Val Lys Lys Val Ala Lys Lys Val Cys Lys Cys Val Lys Lys Ala Val Lys Lys Val Lys Lys Phe

SEQ ID NO. 40: Phe Ala Val Ala Val Lys Ala Val Lys Lys Ala Val Lys Lys Val Lys Lys Ala Val Lys Lys Ala Val Cys Cys Cys

SEQ ID NO. 41: Cys Cys Cys Cys Phe Val Lys Lys Val Ala Lys Lys Val Lys Lys Val Ala Lys Lys Val Ala Lys Val Ala Val Ala Val

SEQ ID NO. 42: Phe Ala Val Ala Val Lys Ala Val Lys Lys Ala Val Lys Lys Val Lys Lys Ala Val Lys Lys Ala Val Ser Ser Ser Ser

SEQ ID NO. 43: Ser Ser Ser Ser Phe Val Lys Lys Val Ala Lys Lys Val Lys Lys Val Ala Lys Lys Val Ala Lys Val Ala Val Ala Val

Chemical modification of lytic peptide analogs offers certain advantages. If the modifications are made in such a way that the peptides retain all or most of their lytic characteristics, then the physiologically active peptides have enhanced stability to proteolysis. With enhanced stability, oral delivery of the peptide is advantageously accommodated without excessive loss of activity due to proteolytic digestion.

EXAMPLE 2

Chemical Modification by Methylation

An exemplary and preferred reaction scheme for reductive alkylation of lysine residue ε-amino group and the N-terminal α-amino group is described below.

The preferred method for reductive alkylation uses pyridine borane as the reducing agent. This reagent is one of a class of reducing agents known as amine boranes. Pyridine borane exhibits a slightly higher reducing capacity than sodium cyanoborohydride, another reducing agent that can be used for the reductive alkylation. Pyridine borane drives the reductive alkylation reaction to complete dimethylation with no monomethyl products when excess reagents are used, as demonstrated by Wong, W. S. D., et al. Analytical Biochemistry 139: 58 (1984). While as much as 25% of cyanoborohydride goes to N-cyanomethyl products, lowering its methylation yield, pyridine borane does not appear to be involved in any such secondary reaction. In addition, sodium cyanoborohydride provides the potential hazard of contaminating the product with cyanide, severely limiting its use in therapeutic and in vivo applications. The alkylation reagent may suitably comprise formaldehyde as a methyl group (methylation) precursor. Shown below are the agents of reductive alkylation, formaldehyde and pyridine borane, the substrate, peptidyl lysine, and the chemical formulae of the reaction scheme species.

FIG. 1: REACTION SCHEME FOR DIMETHYLATION OF PEPTIDYL LYSINE

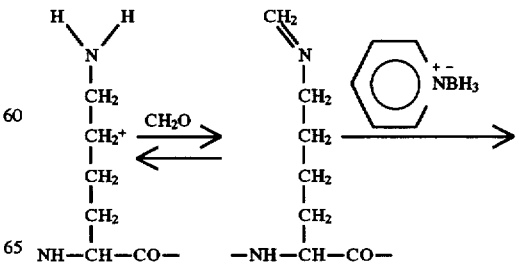

FIG. 1: REACTION SCHEME FOR DIMETHYLATION OF PEPTIDYL LYSINE

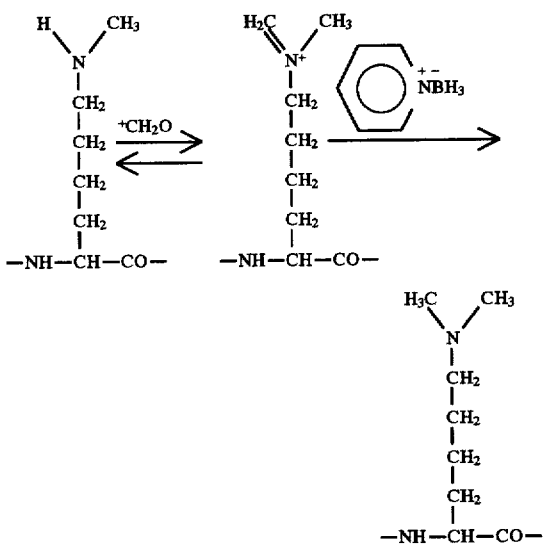

A representative lysine containing peptide, DP-1 (SEQ ID No. 44) (a mellitin analog), was used as the test substrate for the reductive alkylation reaction. DP-1 is a 23-mer lytic peptide with the sequence Phe-Ala-Leu-Ala-Leu-Lys-Ala-Leu-Lys-Lys-Ala-Leu-Lys-Lys-Leu-Lys-Lys-Ala-Leu-Lys-Lys-Ala-Leu. The peptide (20 mg) was dissolved in 1.6 ml 0.2M HEPES buffer (N-2-hydroxyehylpiperazine-N'-2-ethane sulfonic acid), pH 7.0. While the mixture was stirring, 0.2 ml of 1.2M pyridine borane (0.750 concentrated pyridine borane in 5 ml HPLC grade methanol) was added. Next, 0.2 ml of 0.726M formaldehyde (0.6 ml 37% formaldehyde [HCHO] in 10 ml HEPES pH 7.0 buffer) was added to the mixture. A trace (approximately 1 μl) of 1-octanol was included in the reaction volume to control foaming. The reaction volume was then stirred for 2 hours at room temperature. After 2 hours the reaction mixture was titrated to below pH 3.0 with 0.2M HCl. The reaction mixture was then frozen and lyophilized to reduce volume, and the resulting residue was washed 3 times with anhydrous ether to remove the pyridine borane. The reaction residue was reconstituted to approximately 2.0 ml with 0.1M acetic acid and applied to a 2.4 cm×31 cm G-15-120μ Sephadex™ column to purify the reaction product. After the calibrated front eluted from the column (0.1M acetic acid was the elution reagent), 20 ml of eluate containing the product was collected and the eluate was lyophilized to dryness.

The peptide was stored at −20° C. in the presence of a desiccant as their acetate salt. For use in the following examples, modified peptides are dissolved in a saline buffer, pH 7.0, at a concentration of 0.1 mg/ml to 10 mg/ml.

EXAMPLE 3

Determination of Lysyl Dimethylation

The method selected to monitor the level of reductive alkylation is a procedure which provides a spectrophotometric assay of the unsubstituted amino groups (Habeeb, A. F. S. A., Anal. Biochem., 14: 328 [1966]). This procedure uses 2,4,6-trinitrobenzenesulfonic acid (TNBS, picrylsulfonic acid) which reacts with primary amines to form trinitrophenyl (TNP) derivatives, producing a visible yellow color and a UV absorbance maximum at 335 nm. The extent of amino group substitution can therefore be quantified. The procedure is described as follows: Added to the assay tubes is 1.0 ml of 4% $NaHCO_3$, pH 8.5. With mixing, 1.0 ml of peptide standards and unknowns at a concentration of 0.06 to 1.0 mg/ml peptide are added to separate tubes and then 1.0 ml of 0.1% TNBS is added to each tube. The solutions are incubated at 40° C. for 45–60 minutes. After the incubation period, 0.5 ml of 1N HCL is added to the tubes. If necessary, 1 ml of 10% sodium dodecyl sulfate may be added prior to the addition of the acid to prevent precipitation of the peptides. The absorbance at 335 nm is read versus a blank of the reagent mixture minus peptide. As shown in the figure below, the standard curve for detection of unmodified amino groups is essentially linear up to 1.0 mg/ml. The unmodified peptide used for the standard curve is Shiva-11 (SEQ. ID NO: 45), a cecropin analog. The sequence of this 31-mer peptide is: Phe-Ala-Lys-Lys-Leu-Ala-Lys-Lys-Leu-Lys-Lys-Leu-Ala-Lys-Lys-Leu-Ala-Lys-Leu-Ala-Leu -Ala-Leu-Lys-Ala-Leu-Ala-Leu-Lys-Ala-Leu. The TNBS assay standard curve is shown in FIG. 1.

When 0.15 mg of a representative peptide (DP-1), which had been alkylated using the pyridine borane procedure described above, was subjected to the TNBS assay for unmodified amino groups, it yielded an absorbance of 0.007 (compare to standard curve in above figure). This absorbance is essentially zero, meaning that the amino groups on the peptide are fully methylated. In comparison, a reference unmodified peptide sample (Shiva-11) showed an absorbance of 0.474 under the same conditions, indicating a 100% free amino groups. Additionally, the alkylated peptide and its unmodified counterpart were subjected to analytical reversed phase column chromatography and compared with the unmodified peptide. Both scans showed a single peak with no satellite peaks or shoulders.

EXAMPLE 4

In Vitro Lysis of Pathogenic Bacteria

The effect of lytic peptides (SEQ ID NO. 14 and DP-1) were tested against pathogenic bacteria in vitro. In this test, antibiotic resistant clinical isolates of Pseudomonas aeruginosa and Staphylococcus aureus were obtained. The lytic peptide bioassay was performed as described below.

A flask containing 49 ml of nutrient broth was inoculated with 1 ml of an overnight culture of the test bacteria. The culture was allowed to grow to mid-log phase at 37° C. with shaking (approximately 4 hours). When the cells reached the correct density, the cells were transferred to a sterile tube and centrifuged for 10 minutes at 3000 rpm. The pellet was resuspended in 3 ml of phosphate buffer and centrifuged for 10 minutes at 3000 rpm. The pellet was resuspended once again in sufficient (but measured) volume to calculate the absorbance of the suspension at 600 nm. Using the resulting absorbance and a previously constructed growth curve, the required dilution to achieve a concentration of $10^6$ cells/ml was determined.

One micromole of the test peptide was dissolved in 1.0 ml of 0.01% acetic acid to make a 1 mM solution and serial dilutions were made to give a range of peptide concentrations from 10 μM to 1 mM. The test culture tubes for the bioassay contained 800 μl of phosphate buffer, pH 7.0, 100 μl of cells at $10^6$ cells/ml and 100 μl of peptide solution (10 μM to 1 mM). The final concentration of peptide in the assay was from 1 μM to 100 μM. A reaction system minus peptide was included as a control. The tubes were incubated at 37° C. for one hour.

After the incubation period two 1:10 serial dilutions in phosphate buffer were made for each culture(three 1:10 serial dilutions for the control culture). 100 µl of each dilution was spread on a nutrient agar plate, in duplicate and incubated overnight at 37° C. The following day, the number of colonies on the control plates was counted to determine the starting number of cells in the assay tubes. The number of cells surviving the assay in the presence of peptide was also counted. The results are shown in Table 3.

TABLE 3

BACTERICIDAL ACTIVITY OF MODIFIED AND UNMODIFIED PEPTIDES WITH A CLINICAL ISOLATE OF *PSEUDOMONAS AERUGINOSA*

| Peptide Control | µM | Modification* | # of Survivors | % of |
|---|---|---|---|---|
| minus peptide | 0 | | 100,000 | 100 |
| SEQ ID NO. 14 | 10 | | 2 | 0.002 |
| SEQ ID NO. 14 | 10 | m, g | 91 | 0.09 |
| SEQ ID NO. 14 | 1 | | 100,000 | 100 |
| SEQ ID NO. 14 | 1 | m, g | 100,000 | 100 |
| DP-1 | 10 | | 6,607 | 6.6 |
| DP-1 | 10 | m | 2,042 | 2 |
| DP-1 | 1 | | 100,000 | 100 |
| DP-1 | 1 | m | 100,000 | 100 |

*m = methylated lysine residues, g = glyoxylated arginine residues.

This data in this table show that the modification of the peptides does not affect their bacteriolytic activity. Each peptide has a different extent of bacteriolytic activity for a given bacterial species at a given concentration. In general, the peptides in this experiment demonstrated bacteriolytic activity at a concentration of 10 µM, but not at a concentration of 1 µM.

TABLE 4

BACTERICIDAL ACTIVITY OF MODIFIED AND UNMODIFIED PEPTIDES WITH A CLINICAL ISOLATE OF *STAPHYLOCOCCUS AUREUS*

| Peptide Control | µM | Modification* | # of Survivors | % of |
|---|---|---|---|---|
| minus peptide | 0 | | 50,000 | 100 |
| SEQ ID NO. 14 | 10 | | 2,299 | 4.6 |
| SEQ ID NO. 14 | 10 | m, g | 2,818 | 5.6 |
| SEQ ID NO. 14 | 1 | | 50,000 | 100 |
| SEQ ID NO. 14 | 1 | m, g | 50,000 | 100 |
| DP-1 | 10 | | 813 | 1.6 |
| DP-1 | 10 | m | 891 | 1.8 |
| DP-1 | 1 | | 50,000 | 100 |
| DP-1 | 1 | m | 50,000 | 100 |

*m = methylated lysine residues, g = glyoxylated arginine residues.

This data in this table show that the modification of the peptides does not affect their bacteriolytic activity. Each peptide has a different extent of bacteriolytic activity for a given bacterial species at a given concentration. In general, the peptides in this experiment demonstrated activity at a concentration of 10 µM, but not at a concentration of 1 µM.

EXAMPLE 5

Peptide Minimal Inhibitory Concentration

Nutrient broth was inoculated with bacteria and incubated for several hours at 37° C. The density of the incubated broth was then adjusted to a MacFarland 0.5 turbidity standard by adding test broth. The standardized suspension was diluted 1:100. A stock solution of each test antimicrobial agent (DP-1 and methylated DP-1) was prepared in distilled water at a concentration of 1 mg/ml. This stock solution was then diluted with test broth to yield solutions with concentrations of 32 µg/ml, 16 µg/ml, 8 µg/ml, 4 µg/ml, and 2 µg/ml each in 0.9 ml of nutrient broth. To each drug solution 0.1 ml of inoculum was added, and one growth control tube prepared (0.9 ml nutrient broth with 0.1 ml inoculum). For purity check a loopful of the growth control tube was streaked for isolation to a SBAP. All tubes were examined for visible turbidity of growth and the Minimal Inhibitory Concentration (MIC) was determined. The MIC of the tested drug is defined as the lowest concentration of the drug which inhibits the growth of the organism.

TABLE 5

MIC OF A LYTIC PEPTIDE FOR VARIOUS PATHOGENIC BACTERIA

| Clinical Isolate | MIC DP-1 | MIC Methylated DP-1 |
|---|---|---|
| 1. *Staphylococcus aureus* | | |
| A | 16 | >16 |
| B | 8 | >16 |
| C | 8 | >16 |
| D | 16 | >16 |
| E | 16 | >16 |
| 2. Enterococcus species | | |
| 1 | 4 | 16 |
| 2 | 8 | 16 |
| 3 | 4 | 8 |
| 4 | 4 | 16 |
| 5 | 16 | 16 |
| 3. *Pseudomonas aeruginosa* | | |
| 2 | 2 | 2 |
| 15 | 8 | >16 |
| 30 | 4 | 8 |
| 31 | 4 | 8 |
| 32 | 4 | 16 |
| 4. *Xanthomonas sp.* | | |
| 4 | 4 | 2 |
| 5 | 16 | 16 |
| 6 | 4 | 4 |
| 8 | >16 | 16 |

The data in this table show that although the MIC of the methylated and unmethylated peptides vary slightly in some cases, for the most part the differences between the MIC values for the methylated and unmethylated peptides are negligible.

EXAMPLE 6

Fungicidal Activity of Modified and Unmodified Peptides

The following is a description of the formation of alginate beads for fungicide testing. Fungal spores/conidia were suspended in approximately 10 ml of a 20% sterile malt extract solution. The suspension was then filtered through a double layer of cheese cloth (or similar material) in order to remove mycelial fragments. 10 ml of a 2% sodium alginate solution was then added to 10 ml of the fungal spore suspension. Approximately 50 ml of a 10% malt extract solution which contains 1% calcium chloride was poured into a 100 ml beaker. The fungal spore/alginate solution was then added slowly to the calcium chloride solution using a syringe fitted with a fine needle which allows the solution to be added in a drop-wise manner. It is important that the chloride solution is continuously stirred so that the alginate beads do not stick together as they mature. In solution the calcium ions replace the sodium ions, which leads to the formation of the jelly-like beads. The beads are left in the chloride solution for at least 30 minutes before use to ensure that the ion exchange has been completed. The beads formed by this method have a size of about 3 mm in diameter (dependent on the size of the needle used). The beads contain the fungal spores and the necessary nutrients for development. For the test of peptide fungicide activity, two beads are added to 200 μl of the peptide solution in a 96 well microtiter plate. The peptide concentration ranges from 1 mM to 5 μM (1 mM, 0.5 mM, 0.1 mM, 0.05 mM etc.). The assay is visually scored for mycelium growth on Day 2. The result of this assay with unmodified DP-1 and methylated DP-1 m are shown in Table 6 below.

TABLE 6

FUNGICIDAL ACTIVITY OF A LYTIC PEPTIDE

| Peptide | Concentration μM | Fungal Species | Growth |
|---|---|---|---|
| minus peptide | | Pyrolaria | + |
| DP-1 | 5 | Pyrolaria | + |
| DP-1 | 10 | Pyrolaria | + |
| DP-1 | 50 | Pyrolaria | − |
| DP-1m | 5 | Pyrolaria | + |
| DP-1m | 10 | Pyrolaria | +/− |
| DP-1m | 50 | Pyrolaria | − |
| minus peptide | | Botrytis | + |
| DP-1 | 100 | Botrytis | + |
| DP-1 | 500 | Botrytis | +/− |
| DP-1 | 1000 | Botrytis | − |
| DP-1m | 100 | Botrytis | + |
| DP-1m | 500 | Botrytis | + |
| DP-1m | 1000 | Botrytis | + |

The data in the table above show that modification of the peptide by methylation does not have a significant effect on its fungicidal activity, although the peptides themselves have variable activity depending on the fungal species. Both unmodified and methylated DP-1 has fungicidal activity for Pyrolaria at a concentration of 50 μM, and the activity would likely been demonstrated between 10 and 50 μM. In contrast, even at high concentrations, both unmodified and methylated DP-1 lack fungicidal activity for Botrytis.

EXAMPLE 7

Proteolytic Resistance of Modified Peptdies to Trypsin Digestion

A. Modification of the TNBS Assay

In Example 3, a TNBS assay was used to compare unmodified Shiva-11 and modified DP-1 to demonstrate the success of the alkylation reaction. Although this method is adequate for detection of α-amino groups in most peptides, there is at least one application for which it is not. The limitation of the assay was exposed in an attempt to determine the susceptibility of the unmodified peptide, DP-1, to tryptic digestion. In Example 3, unmodified DP-1 was not tested with the TNBS assay.

After incubation at 40° C., the TNBS-treated DP-1 peptide, which had not been subjected to trypsin hydrolysis, produced an opalescence which gradually formed a flocculent precipitate, obscuring the true spectrophotometric value of the sample. According to Habeeb, A. S. F. A., Anal. Biochem. 14: 328 (1966), this problem can be remedied by adding sodium dodecyl sulfate to the assay curer. In this instance, however, the prescribed remedy was not effective. Alteration of the pH of the assay above and below the recommended 8.5 was also not effective in eliminating this problem. Therefore, to complete the experiments for Example 7, it was necessary to revise the TNBS assay to accommodate the anomalous behavior of the unmodified DP-1 peptide.

DP-1 and its methylated form, DP-1 m, were both soluble in pyridine. Furthermore, the reaction of TNBS with primary amines to form the trinitrophenyl (TNP) derivatives could be conducted in pyridine alone without the addition of $NaHCO_3$, pH 8.5, as specified in the original procedure of Example 3. To prevent any opalescence formation, only a small amount of $H_2O$ could be introduced in this assay. Due to the UV absorptive quality of pyridine, absorption for this modified assay was measured at 440 nm in the visible region (the chromophore produces a bright yellow color), rather than the near UV range (335 nm) as specified in the original assay procedure. The TNP derivatization required a much shorter incubation period to reach maximum absorption in the modified assay procedure.

Figure 2:
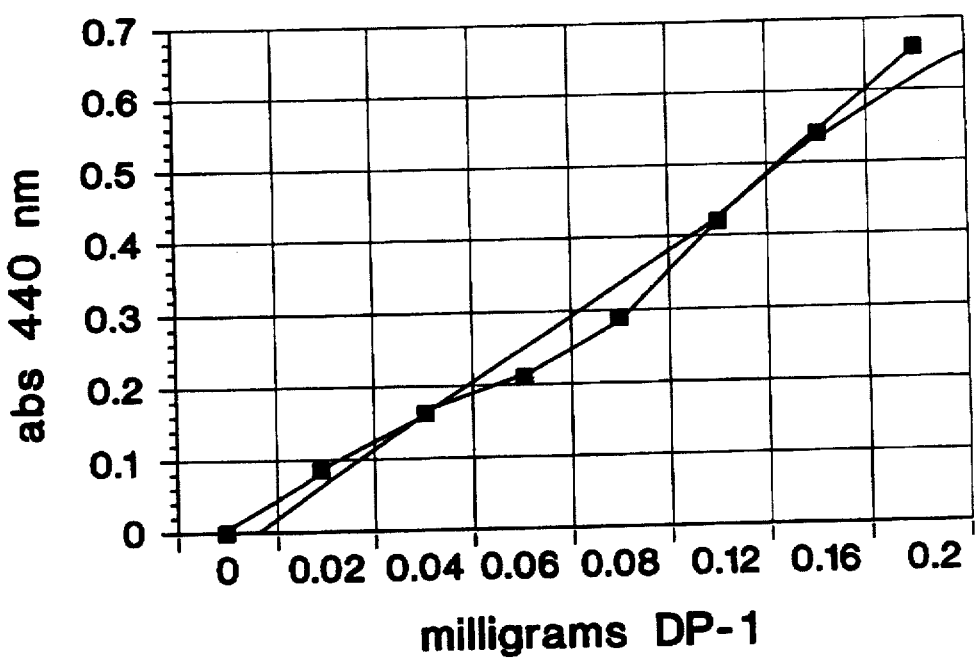
FIG. 2 shows the modified-TNBS assay standard curve for unmodified peptide DP-1.

The modified assay procedure is as follows. Add 2.5 ml purified pyridine (with contaminating aniline removed) into a cuvet. Add a maximum of 0.3 ml of the aqueous peptide solution (0.02 to 0.25 mg). With vigorous mixing, add 0.01 ml of 1% TNBS solution in 1:1 pyridine:$H_2O$. Incubate for 20 minutes at 40° C. Read the absorption at 440 nm and compare to a blank reaction minus peptide. FIG. 2 shows the standard curve for unmodified DP-1 using the modified TNBS assay.

B. Trypsin Digestion and Quantification with the Modified TNBS Assay

In this example, both DP-1 and its alkylated form DP-1 m are exposed to tryptic digestion, and then the amount of digestion is measured by determining the increase in the number of primary amine groups, using the modified TNBS assay. If alkylation of the peptide confers enhanced tryptic digestion resistance, then the modified DP-1 m should show no free amino groups in the TNBS reaction, while the unmodified DP-1 should show an increase in the amount of free primary amine upon digestion with trypsin. DP-1, the peptide used in this study, contains 23 amino acid residues, of which 9 are lysine residues. The peptide contains no arginine. Thus, an unmodified peptide provides a total of 10 primary amine groups before tryptic digestion.

Ten samples (1–10) were prepared. Trypsin was obtained from Sigma Chemical Co. The activity is 9700 units/mg solid. The digestion buffer contains 0.01M HEPES, pH 7.78, 0.05M $CaCl_2$, and 0.10M KCl. The composition of the samples 1–10, respectively is shown in the table below.

TABLE 7

| | TRYPSIN DIGESTION SAMPLES | | | | | | | | | |
|---|---|---|---|---|---|---|---|---|---|---|
| | 1 | 2 | 3 | 4 | 5 | 6 | 7 | 8 | 9 | 10 |
| Hepes Buffer | 0.20 | 0.20 | 0.20 | 0.20 | 0.10 | 0.10 | 0.10 | 0.10 | 0.20 | 0.20 |
| DP-1M 3 mg/ml | 0.10 | 0.10 | | | 0.10 | 0.10 | | | | |

TABLE 7-continued

| | TRYPSIN DIGESTION SAMPLES | | | | | | | | | |
|---|---|---|---|---|---|---|---|---|---|---|
| | 1 | 2 | 3 | 4 | 5 | 6 | 7 | 8 | 9 | 10 |
| DP-1 3 mg/ml | | | 0.10 | 0.10 | | | 0.10 | 0.10 | | |
| Trypsin 1 mg/ml | | | | | 0.10 | 0.10 | 0.10 | 0.10 | 0.10 | 0.10 |

Figure 3:
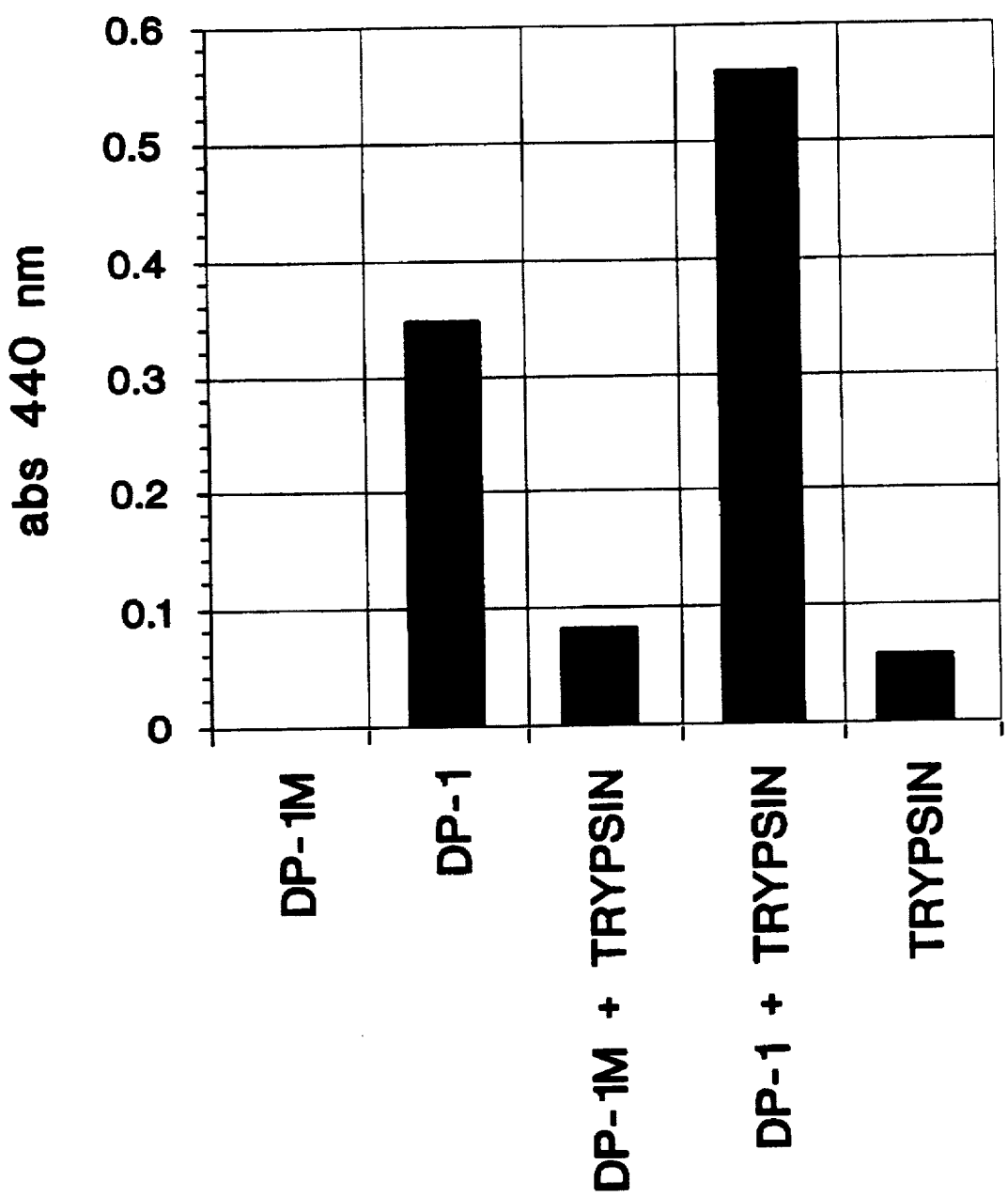
FIG. 3 shows the modified-TNBS assay spectrophotometric data before and after trypsin digestion of unmodified and modified DP-1 peptide.
Figure 4:
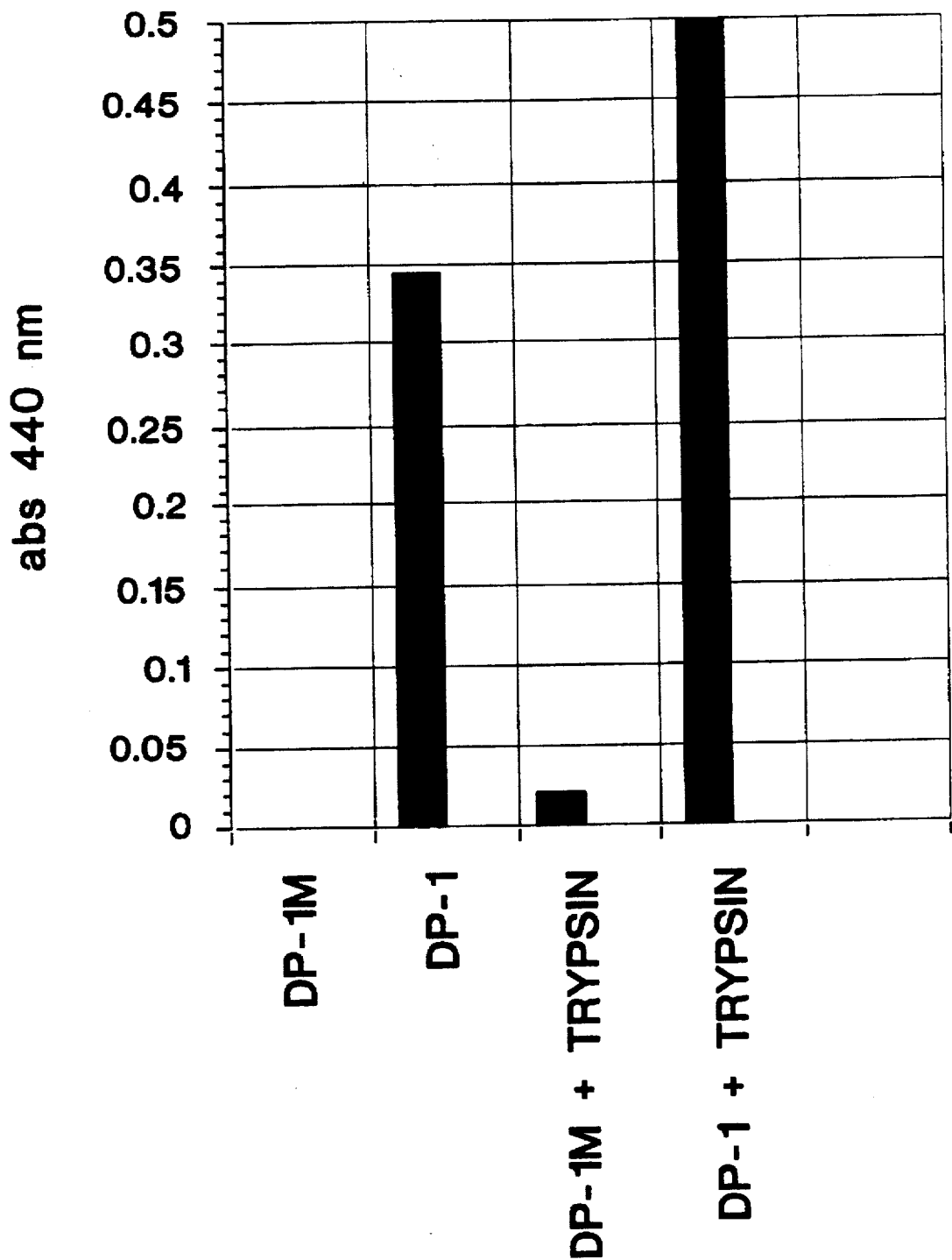
FIG. 4 shows net values of the data from FIG. 3A after subtraction of the trypsin autodigestion control sample from the appropriate experimental samples.

The samples were incubated 30 minutes, after which 0.1 ml aliquots were removed for the modified TNBS assay as described in part A of this example. The TNBS assay shows the amount of free amino groups before and after trypsin digestion. FIGS. 3 and 4 show the results of the trypsin digestion experiment.

The results of the TNBS assay after trypsin digestion demonstrate the expected results. The alkylated DP-1 shows no change in the number of primary amino groups before and after digestion, demonstrating enhanced trypsin digestion resistance. In contrast, the unmodified peptide shows an increase in the number of primary amino groups after tryptic digestion.

While the invention has been described herein, with certain features, and embodiments it will be recognized that the invention may be widely varied, and that numerous other modifications, variations, and other embodiments are possible, and such modification, variations, and other embodiments are to be regarded as being within the spirit and scope of the invention.

What is claimed is:

1. A proteolytic digestion-resistant, non-naturally occurring synthetic lytic peptide comprising a sequence of 12–40 amino acid residues which contains a phenylalanine residue, and one or more alanine, valine, and lysine residues, and optionally contains chemically masked cysteine or serine residues, said lytic peptide selected from the group consisting of SEQ ID NOS. 1–6 and 14–43 in which the ε-amino groups of the lysine residues are methylated to impart enhanced tryptic digestion resistance to the peptide relative to tryptic digestion resistance of the unmethylated synthetic peptide.

2. The proteolytic digestion-resistant, non-naturally occurring synthetic lytic peptide of claim 1, in which the α-amino group of the phenylalanine residue is methylated to impart enhanced chymotryptic digestion resistance to the peptide relative to chymotryptic digestion of the unmethylated peptide.

3. The proteolytic digestion resistant, non-naturally occurring synthetic lytic peptide of claim 1, in which the α-amino group of the N-terminal amino acid residue is methylated to impart enhanced aminopeptidase digestion resistance to the peptide relative to the aminopeptidase digestion resistance of the unmethylated peptide.

4. A method of methylating a non-naturally occurring synthetic lytic peptide whose sequence contains a phenylalanine residue and one or more alanine, valine, and lysine residues and optionally contains chemically masked cysteine or serine residues, said lytic peptide selected from the group consisting of SEQ ID NOS. 1–6 and 14–43, comprising reductively methylating the ε-amino groups of the lysine residues with formaldehyde in the presence of a pyridine-borane reducing agent, thereby conferring enhanced tryptic digestion-resistance to the peptides relative to tryptic digestion-resistance of the unmethylated peptide.

5. The method according to claim 4, further comprising reductively alkylating the α-amino group of the phenylalanine amino acid residue of the peptide with formaldehyde in the presence of a pyridine-borane reducing agent to methylate the α-amino group of the phenylalanine amino acid residue, thereby conferring enhanced chymotryptic digestion-resistance to the peptide relative to chymotryptic digestion-resistance of unmethylated peptides.

6. The method of claim 4, further comprising reductively methylating the α-amino group at the N-terminus of the peptide with a methyl-providing reagent in the presence of a pyridine borane reducing agent, thereby conferring enhanced aminopeptidase digestion-resistance to the peptide relative to aminopeptidase digestion-resistance of the unmethylated peptide.

7. The method of claim 4, further comprising reductively methylating the α-amino group of the N-terminal amino acid and the ε-amino group of lysine amino acid residues of the peptide with a methyl-providing reagent in the presence of a pyridine borane reducing agent, thereby conferring enhanced proteolytic digestion-resistance to the peptide relative to proteolytic digestion-resistance of the unmethylated peptide.

8. The method according to claim 4, comprising reductively methylating the α-amino group of the phenylalanine amino acid residue and the ε-amino group of lysine amino acid residues of the peptide with a methyl-providing reagent in the presence of a pyridine-borane reducing agent, thereby conferring enhanced proteolytic digestion-resistance to the peptide relative to the proteolytic digestion-resistance of the unmethylated peptide.

* * * * *

SEQUENCE LISTING ( 1 ) GENERAL INFORMATION:

( i i i ) NUMBER OF SEQUENCES: 38

( 2 ) INFORMATION FOR SEQ ID NO:1:

( i ) SEQUENCE CHARACTERISTICS:
        ( A ) LENGTH: 27
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 1:

Phe Ala Val Ala Val Lys Ala Val Lys Lys Ala Val Lys Lys Val Lys
 1               5                  10                  15

Lys Ala Val Lys Lys Ala Val Lys Lys Lys Lys
                20                  25

( 2 ) INFORMATION FOR SEQ ID NO: 2:

( i ) SEQUENCE CHARACTERISTICS:
        ( A ) LENGTH: 32
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 2:

Phe Ala Val Ala Val Lys Ala Val Ala Val Lys Ala Val Lys Lys Ala
 1               5                  10                  15

Val Lys Lys Val Lys Lys Ala Val Lys Lys Ala Val Lys Lys Lys Lys
                20                  25                  30

( 2 ) INFORMATION FOR SEQ ID NO: 3:

( i ) SEQUENCE CHARACTERISTICS:
        ( A ) LENGTH: 37
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 3:

```
        Phe   Ala   Val   Ala   Val   Lys   Ala   Val   Ala   Val   Lys   Ala   Val   Ala   Val   Lys
        1                       5                       10                      15

Ala   Val   Lys   Lys   Ala   Val   Lys   Lys   Val   Lys   Lys   Ala   Val   Lys   Lys   Ala
                          20                      25                      30

Val   Lys   Lys   Lys   Lys
                          35
```

( 2 ) INFORMATION FOR SEQ ID NO: 4:

( i ) SEQUENCE CHARACTERISTICS:
        ( A ) LENGTH: 23
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 4:

```
        Phe   Ala   Val   Ala   Val   Lys   Ala   Val   Lys   Lys   Ala   Val   Lys   Lys   Val   Lys
        1                       5                       10                      15

Lys   Ala   Val   Lys   Lys   Ala   Val
                          20
```

( 2 ) INFORMATION FOR SEQ ID NO: 5:

( i ) SEQUENCE CHARACTERISTICS:
        ( A ) LENGTH: 28
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 5:

```
        Phe   Ala   Val   Ala   Val   Lys   Ala   Val   Ala   Val   Lys   Ala   Val   Lys   Lys   Ala
        1                       5                       10                      15

Val   Lys   Lys   Val   Lys   Lys   Ala   Val   Lys   Lys   Ala   Val
                          20                      25
```

( 2 ) INFORMATION FOR SEQ ID NO: 6:

( i ) SEQUENCE CHARACTERISTICS:
        ( A ) LENGTH: 33
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 6:

```
        Phe   Ala   Val   Ala   Val   Lys   Ala   Val   Ala   Val   Lys   Ala   Val   Ala   Val   Lys
        1                       5                       10                      15

Ala   Val   Lys   Lys   Ala   Val   Lys   Lys   Val   Lys   Lys   Ala   Val   Lys   Lys   Ala
                          20                      25                      30

Val
```

( 2 ) INFORMATION FOR SEQ ID NO: 14:

( i ) SEQUENCE CHARACTERISTICS:
        ( A ) LENGTH: 23
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 14:

```
Ala   Val   Lys   Arg   Val   Gly   Arg   Arg   Leu   Lys   Lys   Leu   Ala   Arg   Lys   Ile
1                       5                       10                      15
```

```
Ala  Arg  Leu  Gly  Val  Ala  Phe
               20
```

( 2 ) INFORMATION FOR SEQ ID NO: 15:

( i ) SEQUENCE CHARACTERISTICS:
        ( A ) LENGTH: 27
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 15:

```
Lys  Lys  Lys  Lys  Phe  Val  Lys  Lys  Val  Ala  Lys  Lys  Val  Lys  Lys  Val
 1                   5                        10                       15
Ala  Lys  Lys  Val  Ala  Lys  Val  Ala  Val  Ala  Val
               20                   25
```

( 2 ) INFORMATION FOR SEQ ID NO: 16:

( i ) SEQUENCE CHARACTERISTICS:
        ( A ) LENGTH: 32
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 16:

```
Lys  Lys  Lys  Lys  Phe  Val  Lys  Lys  Val  Ala  Lys  Lys  Val  Lys  Lys  Val
 1                   5                        10                       15
Ala  Lys  Lys  Val  Ala  Lys  Val  Ala  Val  Ala  Lys  Val  Ala  Val  Ala  Val
               20                   25                       30
```

( 2 ) INFORMATION FOR SEQ ID NO: 17:

( i ) SEQUENCE CHARACTERISTICS:
        ( A ) LENGTH: 37
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 17:

```
Lys  Lys  Lys  Lys  Phe  Val  Lys  Lys  Val  Ala  Lys  Lys  Val  Lys  Lys  Val
 1                   5                        10                       15
Ala  Lys  Lys  Val  Ala  Lys  Val  Ala  Val  Ala  Lys  Val  Ala  Val  Ala  Lys
               20                   25                       30
Val  Ala  Val  Ala  Val
               35
```

( 2 ) INFORMATION FOR SEQ ID NO: 18:

( i ) SEQUENCE CHARACTERISTICS:
        ( A ) LENGTH: 23
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 18:

```
Phe  Val  Lys  Lys  Val  Ala  Lys  Lys  Val  Lys  Lys  Val  Ala  Lys  Lys  Val
 1                   5                        10                       15
Ala  Lys  Val  Ala  Val  Ala  Val
               20
```

( 2 ) INFORMATION FOR SEQ ID NO: 19:

( i ) SEQUENCE CHARACTERISTICS:
       ( A ) LENGTH: 28
       ( B ) TYPE: AMINO ACID
       ( C ) TOPOLOGY: LINEAR ( i i ) MOLECULE TYPE: PEPTIDE ( x i ) SEQUENCE DESCRIPTION: SEQ ID NO: 19:

```
Phe Val Lys Lys Val Ala Lys Lys Val Lys Lys Val Ala Lys Lys Val
 1               5                   10                  15
Ala Lys Val Ala Val Ala Lys Val Ala Val Ala Val
             20                  25
```

( 2 ) INFORMATION FOR SEQ ID NO: 20:

( i ) SEQUENCE CHARACTERISTICS:
       ( A ) LENGTH: 33
       ( B ) TYPE: AMINO ACID
       ( C ) TOPOLOGY: LINEAR ( i i ) MOLECULE TYPE: PEPTIDE ( x i ) SEQUENCE DESCRIPTION: SEQ ID NO: 20:

```
 Phe Val Lys Lys Val Ala Lys Lys Val Lys Lys Val Ala Lys Lys Val
  1               5                   10                  15
 Ala Lys Val Ala Val Ala Lys Val Ala Val Ala Lys Val Ala Val Ala
              20                  25                  30
 Val
```

( 2 ) INFORMATION FOR SEQ ID NO: 21:

( i ) SEQUENCE CHARACTERISTICS:
       ( A ) LENGTH: 27
       ( B ) TYPE: AMINO ACID
       ( C ) TOPOLOGY: LINEAR ( i i ) MOLECULE TYPE: PEPTIDE ( x i ) SEQUENCE DESCRIPTION: SEQ ID NO: 21:

```
 Lys Lys Lys Lys Phe Val Lys Lys Val Ala Lys Val Ala Lys Lys Val
  1               5                   10                  15
 Ala Lys Val Ala Lys Lys Val Ala Lys Lys Val
              20                  25
```

( 2 ) INFORMATION FOR SEQ ID NO: 22:

( i ) SEQUENCE CHARACTERISTICS:
       ( A ) LENGTH: 32
       ( B ) TYPE: AMINO ACID
       ( C ) TOPOLOGY: LINEAR ( i i ) MOLECULE TYPE: PEPTIDE ( x i ) SEQUENCE DESCRIPTION: SEQ ID NO: 22:

```
Lys Lys Lys Lys Phe Val Lys Lys Val Ala Lys Val Ala Lys Lys Val
 1               5                   10                  15
Ala Lys Val Ala Lys Lys Val Ala Lys Lys Val Ala Lys Lys Val Ala
             20                  25                  30
```

( 2 ) INFORMATION FOR SEQ ID NO: 23:

( i ) SEQUENCE CHARACTERISTICS:
       ( A ) LENGTH: 37
       ( B ) TYPE: AMINO ACID
       ( C ) TOPOLOGY: LINEAR ( i i ) MOLECULE TYPE: PEPTIDE ( x i ) SEQUENCE DESCRIPTION: SEQ ID NO: 23:

Lys Lys Lys Lys Phe Val Lys Lys Val Ala Lys Val Ala Lys Lys Val
1               5                   10                  15
Ala Lys Val Ala Lys Lys Val Ala Lys Lys Val Ala Lys Lys Val Ala
            20                  25                  30
Lys Val Ala Lys Lys
        35

( 2 ) INFORMATION FOR SEQ ID NO: 24:

( i ) SEQUENCE CHARACTERISTICS:
        ( A ) LENGTH: 23
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 24:

Phe Val Lys Lys Val Ala Lys Val Ala Lys Lys Val Ala Lys Val Ala
1               5                   10                  15
Lys Lys Val Ala Lys Lys Val
            20

( 2 ) INFORMATION FOR SEQ ID NO: 25:

( i ) SEQUENCE CHARACTERISTICS:
        ( A ) LENGTH: 28
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 25:

Phe Val Lys Lys Val Ala Lys Val Ala Lys Lys Val Ala Lys Val Ala
1               5                   10                  15
Lys Lys Val Ala Lys Lys Val Ala Lys Lys Val Ala
            20                  25

( 2 ) INFORMATION FOR SEQ ID NO: 26:

( i ) SEQUENCE CHARACTERISTICS:
        ( A ) LENGTH: 33
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 26:

Phe Val Lys Lys Val Ala Lys Val Ala Lys Lys Val Ala Lys Val Ala
1               5                   10                  15
Lys Lys Val Ala Lys Lys Val Ala Lys Lys Val Ala Lys Val Ala Lys
            20                  25                  30
Lys ( 2 ) INFORMATION FOR SEQ ID NO: 27:

( i ) SEQUENCE CHARACTERISTICS:
        ( A ) LENGTH: 27
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 27:

Phe Val Lys Lys Val Ala Lys Val Ala Lys Lys Val Ala Lys Val Ala
 1               5                   10                  15

Lys Lys Val Ala Lys Lys Val Lys Lys Lys
             20              25

( 2 ) INFORMATION FOR SEQ ID NO: 28:

( i ) SEQUENCE CHARACTERISTICS:
        ( A ) LENGTH: 32
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 28:

Phe Val Lys Lys Val Ala Lys Val Ala Lys Lys Val Ala Lys Val Ala
 1               5                   10                  15

Lys Lys Val Ala Lys Lys Val Ala Lys Lys Val Ala Lys Lys Lys Lys
             20                  25                  30

( 2 ) INFORMATION FOR SEQ ID NO: 29:

( i ) SEQUENCE CHARACTERISTICS:
        ( A ) LENGTH: 37
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 29:

Phe Val Lys Lys Val Ala Lys Val Ala Lys Lys Val Ala Lys Val Ala
 1               5                   10                  15

Lys Lys Val Ala Lys Lys Val Ala Lys Lys Val Ala Lys Val Ala Lys
             20                  25                  30

Lys Lys Lys Lys Lys
         35

( 2 ) INFORMATION FOR SEQ ID NO: 30:

( i ) SEQUENCE CHARACTERISTICS:
        ( A ) LENGTH: 16
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 30:

Phe Lys Val Lys Ala Lys Val Lys Ala Lys Val Lys Lys Lys Lys Lys
 1               5                   10                  15

( 2 ) INFORMATION FOR SEQ ID NO: 31:

( i ) SEQUENCE CHARACTERISTICS:
        ( A ) LENGTH: 21
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 31:

Phe Lys Val Lys Ala Lys Val Lys Ala Lys Val Lys Ala Lys Val Lys
 1               5                   10                  15

Ala Lys Lys Lys Lys
         21

( 2 ) INFORMATION FOR SEQ ID NO: 32:

( i ) SEQUENCE CHARACTERISTICS:
        ( A ) LENGTH: 27
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 32:

```
Phe Lys Val Lys Ala Lys Val Lys Ala Lys Val Lys Ala Lys Val Lys
 1               5                  10                  15
Ala Lys Val Lys Ala Lys Val Lys Lys Lys Lys
            20                  25
```

( 2 ) INFORMATION FOR SEQ ID NO: 33:

( i ) SEQUENCE CHARACTERISTICS:
        ( A ) LENGTH: 12
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 33:

```
Phe Lys Val Lys Ala Lys Val Lys Ala Lys Val Lys
 1               5                  10
```

( 2 ) INFORMATION FOR SEQ ID NO: 34:

( i ) SEQUENCE CHARACTERISTICS:
        ( A ) LENGTH: 17
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 34:

```
    Phe Lys Val Lys Ala Lys Val Lys Ala Lys Val Lys Ala Lys Val Lys
     1               5                  10                  15
    Ala
```

( 2 ) INFORMATION FOR SEQ ID NO: 35:

( i ) SEQUENCE CHARACTERISTICS:
        ( A ) LENGTH: 23
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 35:

```
Phe Lys Val Lys Ala Lys Val Lys Ala Lys Val Lys Ala Lys Val Lys
 1               5                  10                  15
Ala Lys Val Lys Ala Lys Val
            20
```

( 2 ) INFORMATION FOR SEQ ID NO: 36:

( i ) SEQUENCE CHARACTERISTICS:
        ( A ) LENGTH: 16
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 36:

```
Lys Lys Lys Lys Phe Lys Val Lys Ala Lys Val Lys Ala Lys Val Lys
 1               5                   10                  15
```

( 2 ) INFORMATION FOR SEQ ID NO: 37:

( i ) SEQUENCE CHARACTERISTICS:
        ( A ) LENGTH: 21
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 37:

```
Lys Lys Lys Lys Phe Lys Val Lys Ala Lys Val Lys Ala Lys Val Lys
 1               5                   10                  15
Ala Lys Val Lys Ala
              20
```

( 2 ) INFORMATION FOR SEQ ID NO: 38:

( i ) SEQUENCE CHARACTERISTICS:
        ( A ) LENGTH: 27
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 38:

```
Lys Lys Lys Lys Phe Lys Val Lys Ala Lys Val Lys Ala Lys Val Lys
 1               5                   10                  15
Ala Lys Val Lys Ala Lys Val Lys Ala Lys Val
              20                  25
```

( 2 ) INFORMATION FOR SEQ ID NO: 39:

( i ) SEQUENCE CHARACTERISTICS:
        ( A ) LENGTH: 25
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 39:

```
Phe Lys Lys Val Lys Lys Val Ala Lys Lys Val Cys Lys Cys Val Lys
 1               5                   10                  15
Lys Ala Val Lys Lys Val Lys Lys Phe
              20                  25
```

( 2 ) INFORMATION FOR SEQ ID NO: 40:

( i ) SEQUENCE CHARACTERISTICS:
        ( A ) LENGTH: 27
        ( B ) TYPE: AMINO ACID
        ( C ) TOPOLOGY: LINEAR ( i i ) MOLECULE TYPE: PEPTIDE ( x i ) SEQUENCE DESCRIPTION: SEQ ID NO: 40:

```
Phe Ala Val Ala Val Lys Ala Val Lys Lys Ala Val Lys Lys Val Lys
 1               5                   10                  15
Lys Ala Val Lys Lys Ala Val Cys Cys Cys Cys
              20                  25
```

( 2 ) INFORMATION FOR SEQ ID NO: 41:

( i ) SEQUENCE CHARACTERISTICS:
        ( A ) LENGTH: 27

(B) TYPE: AMINO ACID
(C) TOPOLOGY: LINEAR (ii) MOLECULE TYPE: PEPTIDE (xi) SEQUENCE DESCRIPTION: SEQ ID NO:41:

Cys Cys Cys Cys Phe Val Lys Lys Val Ala Lys Lys Val Lys Lys Val
1               5                   10                  15
Ala Lys Lys Val Ala Lys Val Ala Val Ala Val
            20              25

(2) INFORMATION FOR SEQ ID NO: 42:

(i) SEQUENCE CHARACTERISTICS:
    (A) LENGTH: 27
    (B) TYPE: AMINO ACID
    (C) TOPOLOGY: LINEAR (ii) MOLECULE TYPE: PEPTIDE (xi) SEQUENCE DESCRIPTION: SEQ ID NO: 42:

Phe Ala Val Ala Val Lys Ala Val Lys Lys Ala Val Lys Lys Val Lys
1               5                   10                  15
Lys Ala Val Lys Lys Ala Val Ser Ser Ser Ser
            20              25

(2) INFORMATION FOR SEQ ID NO: 43:

(i) SEQUENCE CHARACTERISTICS:
    (A) LENGTH: 27
    (B) TYPE: AMINO ACID
    (C) TOPOLOGY: LINEAR (ii) MOLECULE TYPE: PEPTIDE (xi) SEQUENCE DESCRIPTION: SEQ ID NO: 43:

Ser Ser Ser Ser Phe Val Lys Lys Val Ala Lys Lys Val Lys Lys Val
1               5                   10                  15
Ala Lys Lys Val Ala Lys Val Ala Val Ala Val
            20              25

(2) INFORMATION FOR SEQ ID NO: 44:

(i) SEQUENCE CHARACTERISTICS:
    (A) LENGTH: 23
    (B) TYPE: AMINO ACID
    (C) TOPOLOGY: LINEAR (ii) MOLECULE TYPE: PEPTIDE (xi) SEQUENCE DESCRIPTION: SEQ ID NO: 44:

Phe Ala Leu Ala Leu Lys Ala Leu Lys Lys Ala Leu lys Lys Leu Lys
    1               5                   10                  15
    Lys Ala Leu Lys Lys Ala Leu
                20

(2) INFORMATION FOR SEQ ID NO: 45:

(i) SEQUENCE CHARACTERISTICS:
    (A) LENGTH: 31
    (B) TYPE: AMINO ACID
    (C) TOPOLOGY: LINEAR (ii) MOLECULE TYPE: PEPTIDE (xi) SEQUENCE DESCRIPTION: SEQ ID NO: 45:

Phe Ala Lys Lys Leu Ala Lys Lys Lys Lys Lys Leu Ala Lys Lys Leu

-continued

```
 1              5               10              15
Ala Lys Leu Ala Leu Ala Leu Lys Ala Leu Ala Leu Lys Ala Leu
                20              25              30
```